United States Patent [19]

Gould et al.

[11] 4,406,780

[45] Sep. 27, 1983

[54] SEPARATION AND OXYGEN-ALKYLATION OF PHENOLS FROM PHENOL-CONTAINING HYDROCARBONACEOUS STREAMS

[75] Inventors: Kenneth A. Gould, Berkley Heights; Robert B. Long, Atlantic Highlands, both of N.J.

[73] Assignee: Exxon Research and Engineering Co., Florham Park, N.J.

[21] Appl. No.: 293,968

[22] Filed: Aug. 18, 1981

[51] Int. Cl.³ .................. C07C 37/68; C10G 17/00
[52] U.S. Cl. .................. 208/263; 568/628; 568/630; 568/761
[58] Field of Search .......... 208/263; 585/835, 837, 585/836; 260/692; 568/749, 761, 628, 630

[56] References Cited

U.S. PATENT DOCUMENTS

| | | | |
|---|---|---|---|
| 2,147,256 | 2/1939 | Ipatieff et al. | 568/630 |
| 2,256,612 | 9/1941 | Ellis | 568/630 |
| 2,477,091 | 7/1949 | Rosenwald | 568/630 |
| 2,655,546 | 10/1953 | Stevens et al. | 568/630 |
| 3,071,595 | 1/1963 | Vesely et al. | 568/628 |
| 3,179,703 | 4/1965 | Rieman | 568/749 |
| 3,200,157 | 8/1965 | Buls et al. | 568/628 |
| 3,257,467 | 6/1966 | O'Neill et al. | 568/628 |
| 3,382,283 | 5/1968 | Zundel | 568/628 |
| 3,584,058 | 6/1971 | Hahn | 568/630 |

FOREIGN PATENT DOCUMENTS

| | | | |
|---|---|---|---|
| 374386 | 6/1932 | United Kingdom | 568/761 |
| 960936 | 6/1964 | United Kingdom | 568/761 |
| 1112138 | 1/1967 | United Kingdom | |

OTHER PUBLICATIONS

"Organic Reactions with Boron Fluoride, III. The Condensation of Propylene with Phenol", by F. J. Sowa, H. D. Hinton and J. A. Nieuwland, *Journal of the American Chemical Society*, vol. 54, pp. 1694–1698.

"Boron Fluoride as a Catalyst In Organic Chemistry v. Condensation of Phenol with Amylene, by S. Zavgorodny and K. Fedoseev, *Journal of General Chemistry of the USSR* 16:2006–2010 (1946).

*Primary Examiner*—Delbert E. Gantz
*Assistant Examiner*—O. Chaudhuri
*Attorney, Agent, or Firm*—Henry E. Naylor

[57] ABSTRACT

Properties of phenol-containing hydrocarbonaceous streams are improved by first treating the stream with a $C_1$ to $C_{10}$ alcohol and an acid. If enough alcohol and acid are employed, two liquid phases are formed, an alcohol/acid phase and a hydrocarbonaceous phase. The alcohol/acid phase, which now contains phenols, can be separated and contacted with a $C_1$ to $C_{16}$ olefin or the olefin can be added in situ. In any case, oxygen-alkylation of the phenolic groups occurs.

14 Claims, No Drawings

SEPARATION AND OXYGEN-ALKYLATION OF PHENOLS FROM PHENOL-CONTAINING HYDROCARBONACEOUS STREAMS

BACKGROUND OF THE INVENTION

This invention relates to the separation and oxygen-alkylation of phenols from phenol-containing hydrocarbonaceous streams such as coal liquids.

The presence of phenols in various hydrocabonaceous streams is troublesome. For example, the presence of phenols in liquids produced from coal causes instability of these liquids over a period of time by increasing the viscosity, the color intensity, and causing separation of resinous materials. Moreover, without extensive hydrotreatment, coal liquids are generally not compatible with petroleum liquids of comparable boiling point. Thus, solids separation caused largely by high concentrations of phenols, leads to severe operability problems for coal/petroleum liquid blends. Also, hydrodesulfurization and hydrodenitrogenation of coal liquids are required prior to reforming into motor gasoline. These steps require a very large consumption of hydrogen for phenol-rich coal liquids because of the extensive deoxygenation of phenols to water.

Various methods of removing these troublesome phenols from hydrocarbonaceous streams are taught in the art. For example, it is taught that weakly acidic organic substances such as phenols can be removed from hydrocarbonaceous streams by use of alkali metal or alkaline-earth metal oxides and hydroxides. See U.K. Pat. No. 494,450. It is also taught that phenols react with these oxides and hydroxides resulting in the formation of phenoxide salts which can be easily separated from the purified stream. See U.S. Pat. No. 4,256,568 and French Pat. No. 838,900. Further, it is known that certain phenoxide salts, such as calcium phenoxide, can be heated in the presence of carbon dioxide to yield phenols and calcium carbonate. See Franz Fischer and UDO Ehrahart. Ges. Abhandl. Kenninis Kohle 4,237-63 (1919).

Another method taught for separating phenols from hydrocarbonaceous streams is to wash the stream with large quantities of water or aqueous caustic solutions such as sodium or potassium hydroxide.

Although such methods are practiced on a commercial scale in various industries, there are various drawbacks associated with them. For example, most of the aforesaid methods consume a mol of expensive alkali or alkaline earth metal for each mol of phenol removed. Therefore, there is still a need to develop a more efficient process for removing troublesome phenols from hydrocarbonaceous streams, recovering the phenols in a more efficient and inexpensive way, and converting the phenols to more useful products such as ethers.

SUMMARY OF THE INVENTION

In accordance with the present invention, phenols are separated from phenol-containing hydrocarbonaceous streams and oxygen-alkylated by a method comprising: (a) contacting the stream with (i) one or more $C_1$ to $C_{10}$ aliphatic, alicyclic, or aromaticaliphatic alcohols, and (ii) one or more acids capable of protonating the olefin of step (c) below, in an amount sufficient to produce a two liquid phase system with the stream; (b) separating the resulting acid-alcohol phase, containing a substantial amount of phenols present in the stream, from the treated hydrocarbonaceous phase; and (c) contacting the phenol-containing acid-alcohol phase, at a temperature of about $-20°$ C. to $150°$ C., with one or more $C_2$ to $C_{16}$ olefins. The acids used in the extraction and oxygen-alkylation may be one or more acids selected from Lewis and Bronsted inorganic acids as well as from organic acids.

In preferred embodiments of the present invention the aliphatic alcohol is a $C_1$ to $C_4$ aliphatic alcohol, the acid is selected from the group consisting of sulfuric acid, phosphoric acid, nitric acid, hydrochloric acid, and boron trifluoride; the olefin is a $C_2$ to $C_6$ linear or branched olefin, and the phenol-containing acid alcohol phase is contacted with the olefin at a temperature from about $0°$ C. to about $25°$ C. for an effective amount of time.

In other preferred embodiments of the present invention the phenol-containing hydrocarbonaceous stream is oxygen-alkylated by treating it directly with the olefin and acid, without separating the phenols therefrom.

In yet another embodiment of the invention, oxygen-alkylation can be used to purify a mixed olefin stream by selectively reacting the phenols with only certain components of the olefin stream.

DETAILED DESCRIPTION OF THE INVENTION

Phenol-containing hydrocarbonaceous streams which can be treated in accordance with the invention include, but are not limited to, those streams resulting from the processing of coal and petroleum.

The term phenol-containing hydrocarbonaceous stream means a hydrocarbonaceous stream containing measurable amounts of phenolic compounds in which one or more hydroxyl groups are attached to an aromatic ring and where the aromatic ring may also contain a heteroatom (e.g. nitrogen in a pyridine ring). Non-limiting examples of such phenolic compounds include phenol itself (also known as benzophenol), the cresols, xylenols, resorcinol, naphthols, 8-hydroxyquinoline and 4-hydroxyquinoline. The phenol-containing hydrocarbonaceous stream, exclusive of the phenol compounds, also contains at least 25 wt. % of compounds containing carbon and hydrogen, though other atoms (e.g. nitrogen, oxygen, sulfur) may also be present.

The present invention is not dependent on the method of producing the phenol-containing hydrocarbonaceous stream. For example, any coal liquid containing phenols can be treated regardless of the method of producing the coal liquid. Non-limiting examples of processes for producing coal liquids include pyrolysis, solvent refining, direct hydrogenation with or without a catalyst, catalytic or noncatalytic hydrogenation in the presence of a non-hydrogen donor solvent, and catalytic or noncatalytic liquefaction in the presence of a hydrogen donor solvent.

Although not wishing to be limited hereby, one preferred method for obtaining coal-liquids is the Exxon Donor Solvent (EDS) Process for the liquefaction of coal and described in U.S. Pat. No. 3,617,513 which is incorporated herein by reference. Briefly stated, the EDS Process involves the formation of a slurry of coal in a hydrogen-donor solvent, such as tetralin, maintained at elevated temperatures of about $260°$ C. to $370°$ C. under agitation. Holding the coal at these temperatures causes the coal to disintegrate and dissolve without the breaking of a significant number of coal covalent bonds thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking or depolymerization temperature above 370° C. under a pressure effective to maintain the dispersant slurry substantially in the liquid phase, generally about 350 psig to 3500 psig. In this second temperature stage, the dissolved coal particles are well dispersed in the hydrogen-donor solvent and the chance of a hydrogendonor stabilization of free radicals generated by bond breaking is maximized. At the same time, the chance for free radicals to combine with one another to produce undesirable molecules is minimized. The dispersed slurry is maintained at the elevated temperatures above about 370° C. until a predetermined conversion of the coal is obtained. The liquid, which contain phenols, is then distilled and hydrogenated, the gases drawn off, and the bottoms removed for coking and gasification.

Alcohols suitable for use herein include the $C_1$ to $C_{10}$ aliphatic, alicyclic, and aromatic-aliphatic alcohols, preferably the $C_1$ to $C_4$ aliphatic alcohols, more peferably methanol.

Olefins suitable for use herein include the $C_2$ to $C_{16}$ linear and branched olefins, preferably the $C_2$ to $C_6$ olefins, more preferably the $C_2$ to $C_4$ olefins. Generally about 0.5 to about 40 mols of olefin are employed per mol of phenols of the stream, preferably about 1.5 to 20 mols, more preferably about 1.5 to 10 mols. Of course any excess olefin can be recycled. If the oxygenalkylation is to take place without the formation of two phases, then the olefin used must be miscible in the hydrocarbonaceous stream.

Acids suitable for use herein include those inorganic and organic acids capable of protonating the olefin employed herein. Non-limiting examples of inorganic acids suitable for use herein include those acids selected from the group consisting of sulfuric acid, hydrochloric acid, phosphoric acid, nitric acid, and boron trifluoride. Preferred are sulfuric acid and hydrochloric acid; more preferred is sulfuric acid. Non-limiting examples of organic acids suitable for use herein include trifluoroacetic acid and para-toluene sulfonic acid.

In the practice of the invention, phenols can be separated from the phenol-containing hydrocarbonaceous stream by contacting the stream with either a premixed solution containing both acid and alcohol or with the desired acid and alcohol added sequentially. In either case, the stream is contacted with the acid and alcohol ingredients from about 0° C. to about the boiling point of the alcohol preferably about 0° C. to about 25° C. for an effective amount of time with agitation. Effective amount of time as used above means for at least that amount of time which will allow the separation of a predetermined amount of phenols from the feed stream to the alcohol phase. Factors which contribute to the amount of phenols separated from the stream include the particular acid and alcohol employed, the ratio of acid to alcohol, the overall quantity of acid and alcohol employed, and the temperature at which the stream is contacted with the acid and alcohol. For example, in a single stage operation, one part of 40% $H_2SO_4$ in methanol will extract about 92% of the phenols which are present in one part of a typical coal liquid obtained from liquefaction of bituminous coal.

For effective extraction of phenols with any given acid/alcohol combination, two criteria are required. The first criterion is that two liquid phases form after admixing the acid and alcohol with the hydrocarbonaceous stream. The second criterion is that the acid/alcohol mixture have the capacity to separate the desired percentage of phenols. The amount of acid and alcohol employed for any given phenol extraction is dependent on the desired mol ratio of acid to phenolicoxygen in the stream. For purposes of the invention, it is preferred that the mol ratio be at least that which will remove at least 15 wt. % of phenols from the stream in a single stage extraction.

It will be noted that, if present, carboxylic compounds may also be separated from the hydrocarbonaceous stream when treated in accordance with the present invention. Upon reaction with an olefin as herein described, esters may be produced.

The selection of any particular combination of reactants to achieve the removal of a predetermined amount of phenols can be achieved by routine experimentation by one having ordinary skill in the art and will not be discussed in further detail.

After the hydrocarbonaceous stream is admixed with the acid and alcohol, two liquid phases result. One phase is the hydrocarbonaceous stream and the other phase is comprised of the acid, alcohol, and phenols removed from the stream. Oxygen-alkylation of these phenols can be accomplished by merely adding an olefin to the two phase system or by first physically separating the two phases before adding the olefin to the acid/alcohol/phenol phase.

If the olefin is added to the two phase system, the phenols become oxygen-alkylated and migrate back into the hydrocabonaceous phase—thereby resulting in an upgraded hydrocarbonaceous stream. For example, if the hydrocarbonaceous stream is a coal liquid, it becomes more compatible with a petroleum stream. In the case where the acid/alcohol/phenol phase is first separated from the hydrocarbonaceous phase, before being treated with the olefin, another two phase system results—an acid-alcohol phase and an oxygen-alkylated phenol or ether phase co-mixed with unreacted olefin. This ether phase can now be separated from the acid-alcohol phase by any conventional physical separation method and the acid-alcohol phase can be recycled to the feed stream. The ether phase can be freed of any unreacted olefin and used, for example, as an octane improver for motor fuels if so desired.

If it is desirable that the oxygen-alkylation take place in situ, without the formation of two liquid phases, then only miscible amounts of acid and alcohol, are admixed with the phenol-containing hydrocarbonaceous stream and an appropriate olefin. The admixing is performed at about $-20°$ C. to about 150° C. for an effective amount of time. Preferred is room temperature. Effective amount of time as used here means that amount of time required for the reaction to go to a predetermined level of completion. Generally, times of about 0.25 hr to 4 hr are required for the reaction to go to completion or reach equilibrium at room temperature. Although atmospheric pressure is preferred, higher pressures may be employed.

Another method of oxygen-alkylating the phenols in situ would be (1) to admix the phenol-containing hydrocarbonaceous stream with the olefin, and (2) to pass this mixture over a bed of solid acid catalyst such as, for example, a perfluorinated sulfonic acid resin.

The process of this invention can preferably be conducted by use of a continuous mixer-settler type apparatus wherein the phenol-olefin containing stream and the acid-alcohol mixture are fed to a continuous mixing device with the desired emulsion residence time, thence to a settling drum or chamber to allow phase separation for recycle of the acid-alcohol phase to the mixer as well as continous draw-off from the settler of the treated hydrocarbonaceous phase and a part of the acid-alcohol phase. Obviously, a single state or a multiplicity of mixersettlers in series can be employed.

The stream is preferably agitated to assure sufficient contact of the stream with the acid-alcohol solution. Phenols of the stream separate and enter the alcohol phase and the treated hydrocarbonaceous stream is passed along for further processing, for further contacting with additional amounts of acid-alcohol, or for such treatment as hydrofining. Of course, multi-stage processing can be performed until the desired level of phenol removal is achieved.

The acid-alcohol phase now containing the extracted phenols can, as an alternative to etherification conditions, undergo further treatment to isolate and recover the phenols and recycle the acid-alcohol solution. A non-limiting example of a method suitable for recovering the phenols from the acid-alcohol phase includes extraction with diethyl ether followed by evaporation of the ether of yield phenols and a phenol-free acid-alcohol mixture.

In summary, four embodiments of the present invention have been discussed:

1. Extraction of the phenols into a separate acid/alcohol phase followed by separation of this second phase, followed by addition of an olefin to this phase to accomplish oxygen-alkylation.

2. Addition of sufficient acid-alcohol solution to form a discrete second phase followed by addition of olefin to accomplish oxygen-alkylation. The oxygen-alkylation or etherification is performed without prior isolation of the acid-alcohol phase from the bulk of the hydrocarbonaceous stream. After etherification has been accomplished, the hydrocarbonaceous stream will contain the newly formed ethers and the acid-alcohol phase will contain most of the unreacted phenols. These two immiscible phases can be separated and the acid-alcohol phase can be recycled and/or mixed with fresh olefin if etherification of residual phenols is desired.

3. The desired olefin and an amount of acid insufficient to form a discrete phase can be added directly to the hydrocarbonaceous stream and the oxygen-alkylation performed in situ, i.e. without prior separation of two immiscible phases. For these purposes any organic or inorganic acid capable of catalyzing the oxygen-alkylation reaction may be used. Alcohol, water or other solvents or diluents may be present or absent, depending on the requirement of the particular hydrocarbonaceous stream, olefin, or other reaction conditions.

4. The hydrocarboneous stream may be treated with sufficient amounts of acid and alcohol to form a discrete phase after which the discrete phase can be separated and re-extracted by a suitable solvent which will allow for extraction an subsequent isolation of the phenolics. These isolated phenolics may then be alkylated or used for any other desired purpose.

5. The phenol-containing hydrocarbonaceous stream may be mixed with an appropriate olefin and passed over a fixed bed of a solid acid or slurried and agitated with a solid acid.

The following examples serve to describe, more fully, the present invention. It is understood that these examples in no way serve to limit the true scope of this invention, but rather, are presented for illustrative purposes.

EXAMPLE 1

A 5 gram sample of naphtha obtained from Illinois No. 6 coal by use of the Exxon Donor Solvent Process and containing about 22 wt. % phenolics was washed at room temperature successively with two 2.5 g portions of 40% sulfuric acid in methanol. The treated naphtha was separated from the alcohol phase, neutralized, and dried. It was found that the treated naphtha contained less than 0.1 wt. % of phenolics, wherein all weight percents are based on the total weight of the naphtha.

The naphtha, so treated, will be found to be more stable to the aging effects of air and light.

COMPARATIVE EXAMPLE A

The procedure of Example 1 above was followed except the naphtha was washed with successive 2.5 g portions of 40% sulfuric acid in water. After separation, neutralization, and drying, the treated naphtha was still found to be comprised of about 19.5 wt. % phenolics and was not stable to air and light. This example illustrates the criticality of employing an alcohol, such as methanol, with the inorganic acid for the separation of phenols from a coal liquid.

COMPARATIVE EXAMPLE B

The procedure of Example 1 above was employed except the naphtha was washed with successive 2.5 g portions of 60% methanol in water. After separation and drying, the treated naphtha was found to contain about 1.8 wt. % phenolics and was not stable to air and light. Although a greater percentage of phenolics was removed by use of a methanol-water system versus a sulfuric acidwater system, the sulfuric acid-methanol system of Example 1 above was far superior to both with respect to removal of phenolics from the coal naphtha.

EXAMPLE 2

A 9 g sample of coal naphtha obtained from the Exxon Donor Solvent Process and containing 12.6 wt. % phenols was washed at room temperature successively with two 1 g portions of 40% sulfuric acid in methanol solution. The treated naphtha was found to contain only about 1.5 wt. % phenols, based on the total weight of the naphtha. Thus, between 85% and 95% of the phenols present in the untreated naphtha were removed by the successive washings with 40% sulfuric acid in methanols. Furthermore, the treated naphtha was found to be much more stable than the untreated naphtha with respect to air and light.

The acid-alcohol phases from both washings containing the extracted phenols were combined and contacted with 11.38 g of 2-methyl-2-butene for 1 hour. The acid-alcohol phase was separated from the organic phase, neutralized, and analyzed for oxygenates. The organic phase was reacted for an additional hour, neutralized, stripped of excess olefin, and analyzed for oxygenates.

It was found that the oxygenates present in the acid-alcohol phase were exclusively phenols (which would be further reacted with fresh olefin to yield ethers) whereas of the total oxygenates found in the organic phase, 31 mole % were ethers and the balance phenols. Of course these phenols in the organic phase would be separated by one or more washes with sulfuric acid in methanol and recycled.

EXAMPLE 3

0.15 g of coal liquid was agitated for four hours, at room temperature, with 1.85 g of 2-methyl-2-butene and 0.038 g of 40% $H_2SO_4$ in methanol. The coal liquid was derived from Illinois No. 6 coal by liquefaction using the Exxon Donor Solvent Process and contained about 12 wt. % phenols. The naphtha was analyzed by gas chromatography before and after treatment, and it was found that about 41 mol % of the phenols were oxygen-alkylated by the method of this example. Accordingly, this example demonstrates that the phenols of a coal liquid can by oxygen-alkylated in situ, that is without first separating them from the coal liquid.

EXAMPLE 4

A 20 g sample of coal naphtha obtained from Wyodak coal by the Exxon Donor Solvent Process and containing 1.46 g of phenols was washed at room temperature successively with two 10 gram portions of 40% sulfuric acid in methanol. The treated naptha was analyzed and it was found that 1.35 g or 92% of the phenols was removed. The combined sulfuric acid-methanol-phenol mixture was extracted, at room temperature, successively with three 75 ml portions of diethyl ether. The combined ether layers were neutralized with sodium bicarbonate, filtered, and concentrated to yield 1.32 g of phenols which could then be oxygen-alkylated or used for some other purpose such as a chemical feedstock. This example illustrates one method as a chemical feedstock. This example illustrates one method for separating the phenols from the acid-alcohol after the naphtha is contacted with the acid/methanol mixture.

What is claimed is:

1. A method for removing phenols from phenol-containing coal liquid stream and converting the phenols to ethers, which method comprises:
    (a) contacting the coal liquids with (i) one or more $C_1$ to $C_{10}$ aliphatic, alicyclic, or aromatic-aliphatic alcohols, and (ii) one or more acids capable of protonating the olefin of step (c) below, wherein enough alcohol and acid are employed so that two liquid phases are formed, an alcohol/acid phase which contains phenols extracted from the coal liquids, and a coal liquid phase;
    (b) separating the two phases; and
    (c) contacting the alcohol/acid phase with one or more $C_2$ to $C_{16}$ olefins at a temperature from about $-20°$ C. to about $150°$ C. thereby etherifying a substantial portion of the phenols of the alcohol/acid phase.

2. The method of claim 1 wherein the alcohol is a $C_1$ to $C_4$ aliphatic alcohol.

3. The method of claim 2 wherein the alcohol is methanol or ethanol.

4. The method of claim 3 wherein the acid is an inorganic acid selected from the group consisting of sulfuric acid, phosphoric acid, nitric acid, hydrochloric acid and boron trifluoride.

5. The method of claim 4 wherein the acid is sulfuric acid or hydrochloric acid.

6. The method of claim 4 wherein the olefin is a $C_2$ to $C_6$ olefin.

7. The method of claim 6 wherein the olefin is selected form the group consisting of 2-methyl-2-butene, 1-pentene, 1-butene, 2-butene, isobutylene, propylene, and ethylene.

8. The method of claim 6 wherein the coal liquid stream is contacted with the acid and alcohol at a temperature from about $0°$ C. to about $25°$ C.

9. The method of claim 1 wherein the acid is an organic acid selected from the group consisting of trifluoracetic acid and para-toluene sulfonic acid.

10. A method for converting phenols of phenol containing coal liquid streams to ethers, which method comprises:
    (a) contacting the stream with: (i) one or more $C_1$ to $C_{10}$ alcohols selected from the group consisting of aliphatic, alicyclic, and aromatic-aliphatic alcohols, and (ii) one or more acids capable of protonating the olefin of step (b) below, wherein the stream is contacted with the alcohol and acid in sufficient amounts to cause the formation of two liquid phases, an alcohol/acid phase which contains a substantial amount of phenols extracted from the stream, and a coal liquid phase; and
    (b) contacting the two phase stream of (a) above with one or more $C_2$ to $C_{16}$ olefins at a temperature from about $-20°$ C. to about $150°$ C.

11. The method of claim 10 wherein the acid is an inorganic acid selected from the group consisting of sulfuric acid, phosphoric acid, nitric acid, hydrochloric acid and boron trifluoride.

12. The method of claim 11 wherein the olefin is a $C_2$ to $C_6$ olefin.

13. The method of claim 12 wherein the stream is contacted with the alcohol and acid at a temperature from about $0°$ C. to about $25°$ C.

14. The method of claim 13 wherein the acid is an organic acid selected from the group consisting of trifluoracetic acid and para-toluene sulfonic acid.

* * * * *